United States Patent [19]

Bollinger

[11] 4,311,572

[45] Jan. 19, 1982

[54] PROCESS FOR PREPARING SUBSTITUTED 2-IMINO-4-DIHALOMETHYLENE 1,3-DITHIOLANE COMPOUNDS WHICH ARE USEFUL AS HERBICIDAL ANTIDOTES

[75] Inventor: Frederic G. Bollinger, Creve Coeur, Mo.

[73] Assignee: Monsanto Company, St. Louis, Mo.

[21] Appl. No.: 203,187

[22] Filed: Nov. 3, 1980

Related U.S. Application Data

[63] Continuation-in-part of Ser. No. 960,987, Nov. 15, 1978, Pat. No. 4,231,783.

[51] Int. Cl.$^3$ ............................................. B01J 19/08
[52] U.S. Cl. .................................. 204/158 R; 549/38; 71/90
[58] Field of Search ......... 549/38; 204/158 R, 158 N, 204/158 T

[56] References Cited

U.S. PATENT DOCUMENTS

| | | | |
|---|---|---|---|
| 3,131,509 | 5/1964 | Hoffman | 47/58 |
| 3,139,439 | 6/1964 | Olin | 260/327 |
| 3,189,429 | 6/1965 | Olin | 71/90 |
| 3,389,148 | 6/1968 | Lies | 260/327 |
| 3,449,365 | 6/1969 | Lies | 260/327 |
| 3,449,366 | 6/1969 | Lies | 260/327 |
| 3,484,455 | 12/1969 | Addor | 71/90 |
| 3,755,363 | 8/1973 | Timmons et al. | 71/90 |
| 3,842,096 | 10/1974 | Brand et al. | 260/327 |
| 3,914,428 | 10/1975 | Wilbur et al. | 424/277 |
| 3,928,382 | 12/1975 | Addor et al. | 549/59 X |
| 3,954,801 | 5/1976 | Addor | 260/327 M |
| 4,004,019 | 1/1977 | Brand | 424/277 |
| 4,009,279 | 2/1977 | Addor et al. | 424/277 |
| 4,025,532 | 5/1977 | Lies | 260/327 |
| 4,124,372 | 11/1978 | Pallos et al. | 71/90 |
| 4,231,783 | 11/1980 | Bollinger | 549/38 X |

OTHER PUBLICATIONS

Breslow, et al., "Multi-Sulfur and Sulfur and Oxygen Five and Six-Membered Heterocycles", Part One (1966), pp. 538–546, Interscience Publishers, N.Y.

Hoppe, D., "Metalized Dialkyl Alkyldithioimino Carbonates", CA, 163599e, vol. 83 (1975).

*Primary Examiner*—Joseph Paul Brust
*Attorney, Agent, or Firm*—Patricia A. Coburn; Howard C. Stanley

[57] ABSTRACT

2-Imino-4-dichloromethylene-1,3-dithiolane and its derivatives may be prepared by cyclizing, via photolysis, an appropriate 2,3,3-trihaloalkyl N-substituted dithiocarbamate in the presence of a suitable solvent, as for example, carbon tetrachloride. The 1,3-dithiolane derivatives are useful as herbicidal antidotes.

8 Claims, No Drawings

PROCESS FOR PREPARING SUBSTITUTED 2-IMINO-4-DIHALOMETHYLENE 1,3-DITHIOLANE COMPOUNDS WHICH ARE USEFUL AS HERBICIDAL ANTIDOTES

This application is a continuation-in-part of application Ser. No. 960,987, filed Nov. 15, 1978 which is now U.S. Pat. No. 4,231,783, issued Nov. 4, 1980.

This invention relates to a process for preparing certain substituted 2-imino-4-dihalomethylene-1,3-dithiolane derivatives which have been found to be useful in compositions and methods for reducing herbicidal injury to crop plants. More specifically, the invention relates to a process for preparing the novel 1,3-dithiolane derivatives via photochemical cyclization of certain 2,3,3-trihaloalkyl N-substituted dithiocarbamates, which comprises mixing the dithiocarbamate starting material with a suitable solvent and thereafter exposing the mixture to an ultraviolet light source to effect photo-cyclization of the starting material to produce the 2-imino-4-dihalomethylene-1,3-dithiolane compounds described below.

BACKGROUND OF THE INVENTION

Herbicides are widely used to control weed growth in growing crop plants. Unchecked weed growth is detrimental to the crop plant because weeds compete with crop plants for light, water and various nutrients often resulting in lower crop yields as well as poorer crop quality. Compositions which protect the crop plant from the action of the herbicide, without reducing the herbicidal effectiveness against the weed to be controlled, are very beneficial.

Compounds which are useful in reducing or eliminating crop injury are variously referred to by those skilled in the art as antidotes, safeners or antagonistic agents. The substituted 2-imino-4-dihalomethylene-1,3-dithiolane derivatives described herein are useful as herbicidal safening agents as taught in U.S. Pat. No. 4,231,783, issued to the inventor herein.

Certain other 1,3-dithiolane derivatives, their use and processes for their preparation are known in the art; the following patents are representative of the art in this area.

U.S. Pat. No. 3,449,365 discloses 2-imino-4-alkalidene-1,3-dithiolanes and teaches that said compounds are useful as insecticides, acaricides and nematocides. U.S. Pat. No. 3,389,148 discloses processes for preparing substituted 1,3-dithioles,1,3-dithianes, and 1,3-dithiolanes and the salts thereof which are intermediates in the preparation of phosphorylated imino compounds. U.S. Pat. No. 3,189,429 and 3,139,439 disclose the preparation and herbicidal use of the halide salts of 2-dialkylamino-1,3-dithiolane derivatives. None of the above patents however teach the substituted 2-imino-4-dihalomethylene-1,3-dithiolane compounds described herein or their preparation via the photochemical cyclization process of the present invention.

DESCRIPTION OF THE INVENTION

The invention relates to a process for preparing compounds of the formula

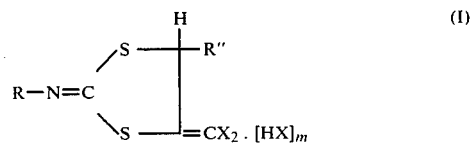

wherein X is chloro or bromo; R is hydrogen, $C_{1-5}$ alkyl or

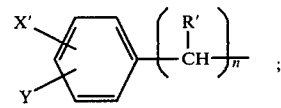

$R'$ is hydrogen or $C_{1-5}$ alkyl; $X'$ and $Y$ independently equal hydrogen, $C_{1-5}$ alkyl, $C_{1-5}$ alkoxy, chloro, bromo, fluoro or iodo; n is 1, 2 or 3; m is 0 or 1; $R''$ is hydrogen or $C_{1-5}$ alkyl; which comprises the steps of:

(a) dissolving a compound having the formula

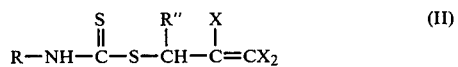

(wherein X, R and $R''$ are defined as in Formula I above) in a suitable solvent;

(b) exposing the mixture to an ultraviolet light source for a time sufficient to effect cyclization of the compound of Formula II to produce the compound of Formula I wherein m is equal to one; and (c) thereafter adding a quantity of base sufficient to neutralize the acid salt to produce the compound of Formula I wherein m is zero.

As used herein the term "alkyl" includes those members including straight and branched chain, having from 1 to 5 carbon atoms inclusive, for example, methyl, ethyl, n-propyl, isopropyl, n-butyl, sec-butyl, tert-butyl, n-pentyl, isopentyl and the like. The term "alkoxy" includes straight and branched chain members having from 1 to 5 carbon atoms, inclusive, for example, methoxy, ethoxy, isopropoxy and the like.

In Formula I wherein m is equal to 1, the compound exists as a salt of a hydrohalic acid, for example, hydrochloric acid or hydrobromic acid. The preferred salt is that derived from hydrochloric acid.

The preferred compounds of Formula I, are those wherein X is equal to chlorine and $R''$ is equal to hydrogen or methyl.

It will be recognized that the hydrohalic salt of the compounds of Formula I is readily neutralized to form the free base by the addition of a sufficient neutralizing amount of organic or inorganic base. Contemplated for use herein are, for example, sodium hydroxide, potassium hydroxide, lithium bicarbonate, sodium bicarbonate, triethyl amine, sodium acetate and the like. Choice of a suitable base is not critical and is within the skill of the art.

In accordance with the process of this invention the dithiocarbamate derivative of Formula II is dissolved in a "suitable solvent". The term "suitable solvent" refers to an organic solvent which is non-reactive with said dithiocarbamate intermediate compound and in which the intermediate dithiocarbamate derivative is soluble. Suitable solvents which may be mentioned are carbon tetrachloride, chloroform, toluene, benzene, xylene, methylene chloride and the like.

Any ultraviolet light source operated from about 350 to about 550 watts is suitable for use in the present invention. The ultraviolet light source which may be mentioned as suitable for use herein is a 450 watt Hanovia high pressure, quartz, mercury-vapor lamp with a PYREX ® filter which absorbs ultraviolet light in the wave length range of from about 270 to about 370 millimicrons. Various types of photochemical equipment are known to those skilled in the art and may be readily purchased from, for example, Ace Glass Inc., 1430 Northwest Boulevard, P.O. Box 688, Vineland, New Jersey 08360.

The process of the present invention may be carried out at temperatures ranging from about 10° C. to 50° C. and at atmospheric pressure. The process of the present invention is preferentially carried out at room temperature.

The process of the present invention may be illustrated as:

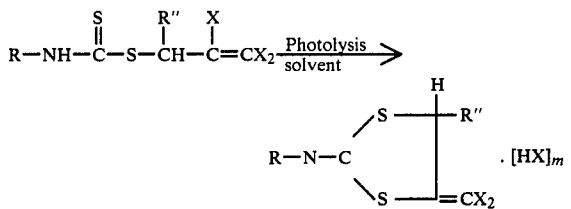

The appropriate 2,3,3-trihaloalkyl N-substituted dithiocarbamate dissolved in a suitable solvent, e.g., carbon tetrachloride, chloroform, toluene or the like is placed in a photochemical reaction vessel and sparged with nitrogen. The resulting mixture is thereafter exposed to an ultraviolet light source supplying ultraviolet radiation in the wave length range of from about 270 to about 370 millimicrons for a period of time to complete cyclization, usually about 30 minutes to about 4 hours. The nirogen sparge is continued throughout the reaction.

The 2,2,3-trihaloalkyl N-substituted dithiocarbamate compounds used as intermediates starting materials in the process of the present invention may be prepared by reacting approximately equimolar portions of an appropriate substituted amine with carbon disulfide and thereafter adding to this mixture, with gentle heating, a tetrahalopropene compound. Example 1 below describes in detail the preparation of 2,3,3-trichloroalkyl-N-(α-methylbenzyl)dithiocarbamate, a typical intermediate compound.

To facilitate further understanding of the process of the present invention, the following illustrative examples are presented. These examples are not intended to be taken as limitative of the invention.

EXAMPLE 1

2,3,3-Trichloroallyl N-(α-methylbenzyl)dithio carbamate

A two-phase mixture containing 6.0 g (0.0495 mol) dl-α-methylbenzylamine and 8.0 g (0.05 mol) 25% NaOH in 50 ml water was stirred rapidly at 0°–10° C. while 4.0 g (0.05 mol) carbon disulfide was added dropwise over 2–3 minutes. The mixture was stirred and allowed to warm to 20° C. over a one hour period. To this stirred slurry was added 9.0 g (0.05 mol) 1,1,2,3-tetrachloropropene in one portion. A yellow two phase mixture resulted and the temperature slowly rose to a maximum of 28° C. The mixture was heated gently to 45°–50° C. for three hours, then let cool and extracted with 300 ml ethyl ether. The ether solution was washed with two, 50 ml portions of water, treated with activated charcoal and MgSO$_4$, filtered through Hy-flo and evaporated in vacuo below 40°/<1 torr to give 14.9 g (88%) of a light orange oil.

Anal. Calc'd for $C_{12}H_{12}Cl_3NS_2$: N, 4.11; Cl, 31.2; S, 18.8; Found: N, 4.26; Cl, 31.4; S, 18.8.

EXAMPLE 2

Benzylamine, N-[4-(dichloromethylene)-1,3-dithiolan-2-ylidene] Hydrochloride

A solution containing 16.35 g (0.05 mol) of 2,3,3-trichloroallyl N-benzyldithiocarbamate in 50 ml of carbon tetrachloride was placed in a photochemical reaction vessel fitted with a fritted disc bottom for sparging N$_2$ through the solution. A 450-watt, Hanovia high pressure mercury lamp, with a Pyrex filter, was inserted into the water-cooled quartz immersion well. The solution was agitated with a gentle stream of N$_2$ bubbles and photolyzed for 35 minutes. The CCl$_4$ was decanted off leaving a solid which was triturated with benzene, collected by filtration and air dried to give 7.2 g mp 158°–161° C. A sample was recrystallized from CHCl$_3$/CCl$_4$ to give off-white crystals, mp 152°–159° C., yield 44%.

Anal. Calc'd for $C_{11}H_9Cl_2NS_2.HCl$: N, 4.29; Cl, 32.6; S, 19.6; N.E., 327; Found: N, 4.32; Cl, 32.4; S, 19.8; N.E., 321.

EXAMPLE 3

Benzylamine-,α-methyl-N-[(4-(dichloromethylene)-1,3-dithiolan-2-ylidene] Hydrochloride This compound was prepared according to the procedure described in Example 2 except that 2,3,3-trichloroallyl-N-α-methylbenzyl dithiocarbamate was used. A solid was obtained in 47.5% yield, mp 152°–153° C.

Anal. Calc'd for $C_{12}H_{11}Cl_2NS_2.HCl$: N, 4.11; Cl, 31.2; S, 18.8; Found: N, 4.06; Cl, 31.3; S, 19.0.

EXAMPLE 4

Benzylamine-,α-methyl-N-[4-(dichloromethylene)-1,3-dithiolan-2-ylidene]

A slurry consisting of 4.8 g (0.014 mol) of the hydrochloride salt of Example 3, in 60 ml of water was stirred and made slightly basic with triethylamine. The mixture was extracted with 50 ml ethyl ether. The separated ether solution was washed with 2, 25 ml portions of cold water, dried over MgSO$_4$ and evaporated in vacuo at 50°/<0.5 torr to give 4.1 g light amber oil. The oil which solidified on standing at room temperature was recrystallized from pet ether, mp 39°–40.5° C., yield 99%.

Anal. Calc'd for $C_{12}H_{11}Cl_2NS_2$: N, 4.60; Cl, 23.3; S, 21.1; Found: N, 4.71; Cl, 23.3; S, 21.1.

EXAMPLE 5

Benzylamine,α-isopropyl N-[4-dichloromethylene) 1,3-dithiolan-2-ylidene]

A solution of 35.6 g (0.097 mol) 2,3,3-trichloroallyl N-(α-isopropyl)benzyldithiocarbamate in 100 ml chloroform was photolyzed for 2½–3 hours. After evaporation of the chloroform the residue was treated with benzene but no crystalline hydrochloride salt formed. The benzene solution was diluted with ethyl ether and the organic solution treated with dilute NaOH. The organic layer was then dried and evaporated to give 29.3 g red amber oil. A 10 g portion of this oil was purified by HPLC (High performance liquid chromatography) on silica gel using toluene to give 5.0 g of the pure free base, yield 45.7%.

Anal. Calc'd for $C_{14}H_{15}Cl_2NS_2$: N, 4.21; Cl, 21.3; S, 19.3; Found: N, 4.16; Cl, 21.4; S, 19.4.

EXAMPLE 6

Isopropylamine, N-[4-(dichloromethylene) 1,3-dithiolan-2-ylidene] Hydrochloride

A solution containing 10.0 g (0.036 mol) 2,3,3-trichloroallyl N-isopropyldithiocarbamate in 100 ml $CCl_4$ was photolyzed for 0.5 hour. The solid product was collected by filtration and air dried to give 3.8 g, mp 149°–154° C. Crystallization from $CHCl_3/CCl_4$ gave 2.5 g, mp 155°–157° C., yield 38%.

Anal. Calc'd for $C_7H_9Cl_2NS_2.HCl$: N, 5.03; Cl, 38.2; S, 23.0; Found: N, 5.05; Cl, 37.8; S, 22.8.

EXAMPLE 7

1,3-Dithiolane-,2-imino-4-dichloromethylene Hydrochloride

A solution containing 4.8 g (0.02 mol) 2,3,3-trichloroallyl dithiocarbamate in 75 mls of chloroform was photolyzed for one hour. The chloroform was drawn off through the bottom sintered glass frit and the solid residue triturated with fresh chloroform again filtered and the recovered solids air dried to give 3.3 g, mp 180° C. (dec.) sinters at 120° C. Crystallization from MeOH/ethyl ether gave a light tan powder, mp 187° C. (dec.).

Anal. Calc'd for $C_4H_3Cl_2NS_2.HCl$: N, 5.92; Cl, 45.0; S, 27.1; Found: N, 5.94; Cl, 44.2; S, 26.7.

Following the procedures described in Examples 2–7, other N-(4-dichloromethylene)-1,3-dithiolanes of the invention were prepared. Table I describes these compounds in greater detail.

TABLE I

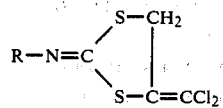

| Example No. | Empirical | R | Analysis Calc'd | Found | Solvent | Mp °C. | % Yield |
|---|---|---|---|---|---|---|---|
| 8 | $C_5H_5Cl_2NS_2.HCl$ | $CH_3$— | N, 5.59; Cl, 42.4; S, 25.6; | 5.56 42.6 25.7 | $CCl_4$ | 193–194 | 46 |
| 9 | $C_{12}H_{10}Cl_3NS_2.HCl$ | 3-Cl-C6H4-CH(CH3)- | N, 3.73; Cl, 37.8; S, 17.1, | 3.78 37.7 17.1 | $CCl_4$ | 144–149 | 28.5 |
| 10 | $C_{13}H_{13}Cl_2NS_2.HCl$ | 4-CH3-C6H4-CH(CH3)- | N, 3.95; Cl, 30.0; S, 18.1; | 3.89 30.0 18.1 | $CHCl_3$ | 152.5–155.0 | 43 |
| 11 | $C_{16}H_{19}Cl_2NOS_2.HCl$ | 4-CH3O-C6H4-C(CH3)2- | N, 3.39; Cl, 25.8; S, 15.5; | 3.36 25.8 15.5 | $CHCl_3$ | 147–152.5 | 29.5 |
| 12 | $C_{13}H_{13}Cl_2NS_2$ | 4-CH3-C6H4-CH(CH3)- | N, 4.40; Cl, 22.3; S, 20.1; | 4.43 22.4 20.1 | $CHCl_3$ | Oil | 94 |
| 13* | $C_{16}H_{19}Cl_2NS_2$ | C6H5-CH((CH2)4CH3)- | N, 3.89; Cl, 19.7; S, 17.8; | 3.80 19.6 17.7 | $CHCl_3$ | Oil | 62 |

*Isolated by HPLC.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

I claim:

1. A process for preparing compounds of the formula

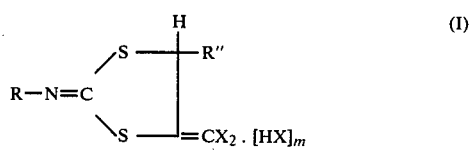

wherein X is chloro or bromo; R is hydrogen, $C_{1-5}$ alkyl, or

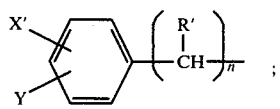

R' is hydrogen or $C_{1-5}$ alkyl; X' and Y independently equal hydrogen, $C_{1-5}$ alkyl, $C_{1-5}$ alkoxy, chloro, bromo, fluoro or iodo; N is 1, 2 or 3; m is 0 or 1; R'' is hydrogen or $C_{1-5}$ alkyl; which comprises the steps of:

(a) dissolving a compound having the formula

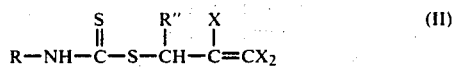

(II)

(wherein X, R and R" are defined as in Formula I above) in an organic solvent which is non-reactive with the compound of Formula II and in which the compound of Formula II is soluble;

(b) exposing the mixture to an ultraviolet light source for a time sufficient to effect cyclization of the compound of Formula II to produce the compound of Formula I; wherein the reaction temperature is maintained at from 10° C. to 50° C. and wherein the reaction is carried out at atmospheric pressure.

2. A process according to claim 1 wherein X is chloro and wherein R" is hydrogen or methyl.

3. A process according to claim 2 wherein R is

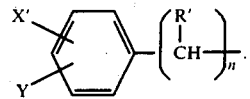

4. A process according to claim 3 wherein n is 1.

5. A process according to claim 1 wherein said solvent is selected from the group consisting of carbon tetrachloride, chloroform and toluene.

6. A process according to claim 1 wherein the temperature of said reaction is maintained at room temperature.

7. A process according to claim 1 wherein said reaction time is from about 30 minutes to about 4 hours.

8. A process according to claim 1 wherein the compounds of Formula I are treated with a quantity of base sufficient to neutralize the acid salt to produce the free base.

* * * * *